United States Patent
Shrum et al.

(10) Patent No.: US 10,500,079 B2
(45) Date of Patent: Dec. 10, 2019

(54) PRELOADED BRANCH WIRE LOOP CONSTRAINT

(71) Applicant: Cook Medical Technologies LLC, Bloomington, IN (US)

(72) Inventors: Alexander Shrum, West Lafayette, IN (US); Brandon Tran, West Lafayette, IN (US); Charles L. Baxter, West Lafayette, IN (US); Jarin A. Kratzberg, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 252 days.

(21) Appl. No.: 15/336,229

(22) Filed: Oct. 27, 2016

(65) Prior Publication Data
US 2018/0116838 A1   May 3, 2018

(51) Int. Cl.
*A61F 2/954* (2013.01)
*A61F 2/07* (2013.01)
(Continued)

(52) U.S. Cl.
CPC .............. *A61F 2/954* (2013.01); *A61F 2/07* (2013.01); *A61F 2002/061* (2013.01); *A61F 2002/9505* (2013.01); *A61F 2002/9522* (2013.01)

(58) Field of Classification Search
CPC ...... A61F 2/07; A61F 2/954; A61F 2002/061; A61F 2002/9505; A61F 2002/9522
See application file for complete search history.

(56) References Cited

U.S. PATENT DOCUMENTS

| 4,502,159 A | 3/1985 | Woodroof et al. |
| 4,675,361 A | 6/1987 | Ward, Jr. |

(Continued)

FOREIGN PATENT DOCUMENTS

| EP | 2564812 A1 | 3/2013 |
| EP | 3064173 A1 | 9/2016 |

(Continued)

OTHER PUBLICATIONS

Manning, Brian J., et al., "Preloaded Fenestrated Stent-Grafts for the Treatment of Juxtarenal Aortic Aneurysms," *J. Endovasc Ther*, 2010: vol. 17, pp. 449-455.
(Continued)

*Primary Examiner* — Jocelin C Tanner
(74) *Attorney, Agent, or Firm* — Brinks Gilson & Lione

(57) ABSTRACT

An endoluminal prosthesis assembly includes a delivery system having an introduction end, an operator end, and a stent graft retention region. An endoluminal prosthesis is disposed at the stent graft retention region. The prosthesis comprises a tubular body, an inner lumen extending between proximal and distal ends of the tubular body, at least one fenestration disposed in a sidewall of the body, and an internal branch at least partially formed with the sidewall of the body and disposed in parallel alignment with the prosthesis. A guide wire having a first end and a second end is pre-loaded with the prosthesis in the delivery system. At least a portion of the guide wire is disposed within the internal branch and the inner lumen of tubular body of the prosthesis prior to delivery of the prosthesis and during delivery and deployment of the prosthesis. The second end of the guide wire extends distally from the distal opening of the tubular body, and the first end of the guide wire extends through the internal branch and the at least one fenestration such that a portion of the guide wire is externally disposed (Continued)

relative to the prosthesis. The externally disposed portion of the guide wire is bent back on itself to form an externally disposed loop.

16 Claims, 8 Drawing Sheets

(51) Int. Cl.
*A61F 2/95* (2013.01)
*A61F 2/06* (2013.01)

(56) References Cited

U.S. PATENT DOCUMENTS

| | | | |
|---|---|---|---|
| 4,861,830 A | | 8/1989 | Ward, Jr. |
| 4,902,508 A | | 2/1990 | Badylak et al. |
| 5,017,664 A | | 5/1991 | Grasel et al. |
| 5,380,304 A | | 1/1995 | Parker |
| 5,387,235 A | | 2/1995 | Chuter |
| 5,733,337 A | | 3/1998 | Carr et al. |
| 5,904,648 A | * | 5/1999 | Arndt ................ A61B 1/0056 |
| | | | 600/120 |
| 6,099,548 A | | 8/2000 | Taheri |
| 6,206,931 B1 | | 3/2001 | Cook et al. |
| 6,358,284 B1 | | 3/2002 | Fearnot et al. |
| 6,379,710 B1 | | 4/2002 | Badylak |
| 6,589,227 B2 | | 7/2003 | Sonderskov Klint |
| 6,666,892 B2 | | 12/2003 | Hiles et al. |
| 6,752,826 B2 | | 6/2004 | Holloway et al. |
| 6,939,377 B2 | | 9/2005 | Jayaraman et al. |
| 7,025,758 B2 | | 4/2006 | Klint |
| 8,747,455 B2 | | 6/2014 | Greenberg |
| 9,101,455 B2 | | 8/2015 | Roeder et al. |
| 2001/0034514 A1 | | 10/2001 | Parker |
| 2002/0032408 A1 | | 3/2002 | Parker et al. |
| 2002/0187288 A1 | | 12/2002 | Lim et al. |
| 2003/0149471 A1 | | 8/2003 | Briana et al. |
| 2004/0230287 A1 | | 11/2004 | Hartley et al. |
| 2006/0064036 A1 | * | 3/2006 | Osborne ................ A61M 25/01 |
| | | | 600/585 |
| 2006/1555302 | | 7/2006 | Sisken et al. |
| 2007/0299499 A1 | * | 12/2007 | Hartley ................ A61F 2/962 |
| | | | 623/1.11 |
| 2008/0064988 A1 | * | 3/2008 | Carter ................ A61M 25/09 |
| | | | 600/585 |
| 2008/0109065 A1 | | 5/2008 | Bowe |
| 2008/0255656 A1 | * | 10/2008 | Saeed ................ A61F 2/954 |
| | | | 623/1.12 |
| 2010/0198328 A1 | | 8/2010 | Hartley et al. |
| 2010/0204770 A1 | | 8/2010 | Mas et al. |
| 2011/0034804 A1 | * | 2/2011 | Hubregtse ........ A61B 17/00234 |
| | | | 600/433 |
| 2012/0041535 A1 | | 2/2012 | Huser et al. |
| 2012/0130472 A1 | | 5/2012 | Shaw |
| 2013/0123907 A1 | | 5/2013 | Roeder et al. |
| 2013/0131777 A1 | * | 5/2013 | Hartley ................ A61F 2/07 |
| | | | 623/1.11 |
| 2014/0257453 A1 | | 9/2014 | Roeder |
| 2014/0277330 A1 | | 9/2014 | Roeder |
| 2015/0012080 A1 | | 1/2015 | Barrand |

FOREIGN PATENT DOCUMENTS

| | | |
|---|---|---|
| WO | WO98/22158 | 5/1998 |
| WO | WO 2012/065625 A1 | 5/2012 |
| WO | WO 2014/172501 A2 | 10/2014 |

OTHER PUBLICATIONS

European Search Report for EP Application No. 17275163.8 dated Mar. 14, 2018, 11 pages.

* cited by examiner

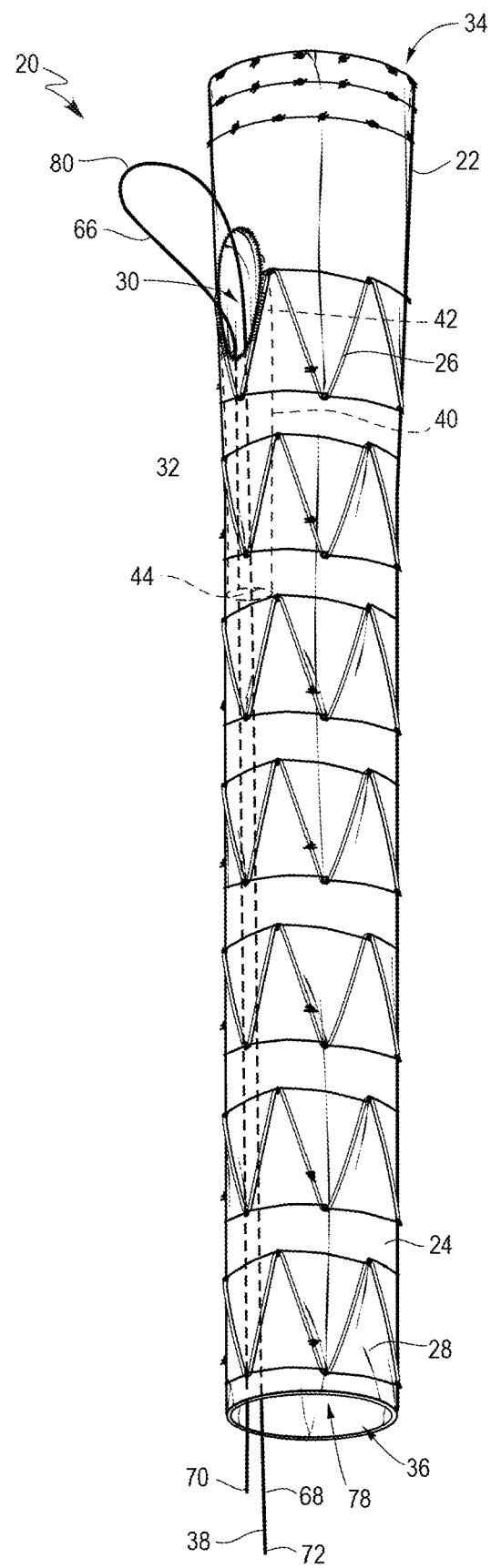

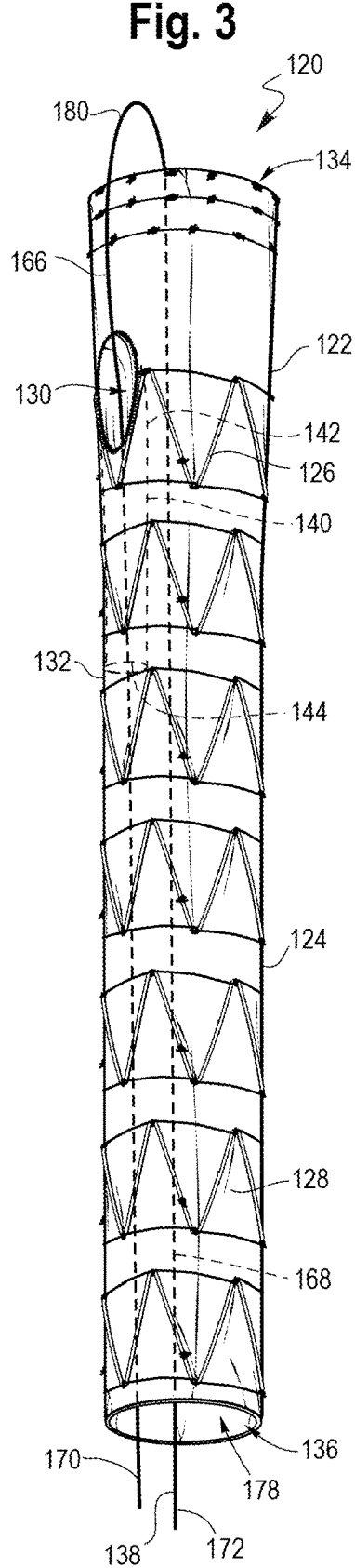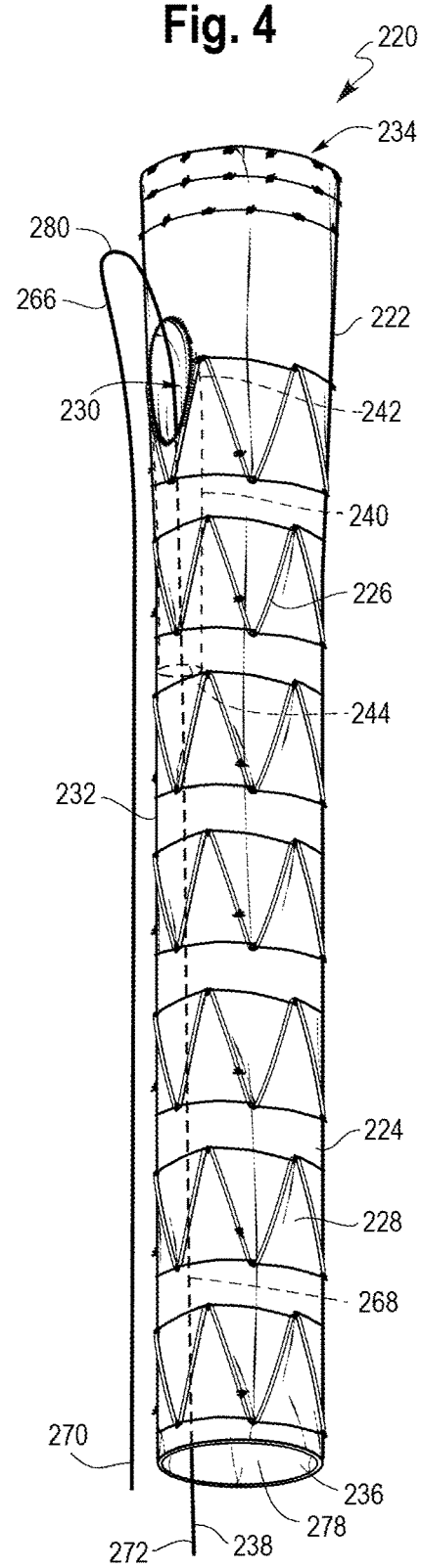

PRELOADED BRANCH WIRE LOOP CONSTRAINT

BACKGROUND

1. Field of the Invention

The present invention generally relates to medical treatment and, in particular, to devices, systems, and methods for delivering and deploying endoluminal medical devices.

2. Background Information

The deployment of a medical device, such as an endoluminal prosthesis, into the vessel of a patient from a remote location by the use of a catheter delivery device is generally known. A catheter delivery device carrying an endoluminal prosthesis is delivered into a vessel over a guide wire previously placed within the vessel. Once the catheter device is positioned, the prosthesis is released and expanded to repair the vessel.

An endoluminal prosthesis can be used, for example, to repair diseased and/or damaged conduits, such as blood vessels, the esophagus, the trachea, and the like. Endoluminal prostheses have become a popular option for treating damage and disease to blood vessels, such as abdominal aortic and/or thoracic aneurysms.

In some cases, it may be necessary to deploy an endoluminal prosthesis in a major vessel (e.g., the aorta) at or near an intersecting branch vessel (e.g., innominate, carotid, subclavian, celiac, SMA, and renal arteries). In these cases, an endoluminal prosthesis may be provided with one or more fenestrations so that the prosthesis can overlap the branch vessels without blocking flow to these vessels. Once the prosthesis is placed in the main vessel, it may be necessary to provide interventional access between the main vessel and a branch vessel. For example, a physician may desire to deliver additional interventional catheters carrying balloons, stents, grafts, imaging devices, and the like through the fenestration.

Before such a catheter device can be delivered through the fenestration to a target vessel; however, a guide wire must be provided and delivered through the fenestration to the target vessel. Typically, this requires multiple steps. First, the physician must deliver and navigate a set of catheters and wires to pass a guide wire through the fenestration. Once the fenestration is cannulated, the physician must then deliver and navigate a separate set of catheters and wires to pass a guide wire into the target vessel. The present invention is directed to devices, systems, and methods for delivering and deploying a prosthesis comprising a fenestration, where such devices, systems, and methods include an endoluminal prosthesis comprising a fenestration with a preloaded guide wire having a looping configuration.

BRIEF SUMMARY

In a first aspect of the invention, an endoluminal prosthesis assembly comprises a delivery system having an introduction end, an operator end, and a stent graft retention region. The assembly also includes an endoluminal prosthesis disposed at the stent graft retention region. The prosthesis comprises a tubular body, an inner lumen extending between proximal and distal ends of the tubular body, at least one fenestration disposed in a sidewall of the tubular body between the proximal and distal ends, and an internal branch at least partially formed with the sidewall of the tubular body and disposed in parallel alignment with the prosthesis. The proximal end of the tubular body is toward the introduction end and the distal end of the tubular body is toward the operator end. The assembly further includes a guide wire pre-loaded with the prosthesis in the delivery system. At least a portion of the guide wire between a first end and a second end is disposed within the internal branch and the inner lumen of the prosthesis prior to delivery of the prosthesis and during delivery and deployment of the prosthesis. The second end of the guide wire extends distally from the distal opening of the tubular body, and the first end of the guide wire extends through the internal branch and the at least one fenestration such that a portion of the guide wire is externally disposed relative to the prosthesis. The externally disposed portion of the guide wire is bent back on itself to form an externally disposed loop. After forming the loop, the first end of the guide wire re-enters the tubular body of the prosthesis such that the first end of the guide wire is disposed internally relative to the prosthesis.

In a feature of the first aspect, the first end of the guide wire is attached by a releasable fastening device to an interior surface of the tubular body during delivery and deployment of the prosthesis. With regard to this feature, the releasable fastening device is a suture.

In another feature of the first aspect, the first end of the guide wire re-enters the tubular body of the prosthesis through the proximal opening of the tubular body. In a further feature, the first end of the guide wire re-enters the tubular body of the prosthesis through the at least one fenestration from which it exited.

In an additional feature of the first aspect, the at least one fenestration comprises two or more fenestrations. In yet another feature, the loop has a length of about 3 cm to about 6 cm. In a further feature, the loop has a length greater than 3 cm and less than 8 cm. In still another feature, the guide wire comprises nitinol.

In another aspect of the invention, an endoluminal prosthesis assembly comprises a delivery system having an introduction end, an operator end, and a stent graft retention region. An endoluminal prosthesis is disposed at the stent graft retention region. The prosthesis comprises a tubular body, an inner lumen extending between proximal and distal ends of the tubular body, at least one fenestration disposed in a sidewall of the tubular body between the proximal and distal ends, and an internal branch at least partially formed with the sidewall of the tubular body and disposed in parallel alignment with the prosthesis. The proximal end of the tubular body is toward the introduction end and the distal end of the tubular body is toward the operator end. A guide wire is pre-loaded with the prosthesis in the delivery system. At least a portion of the guide wire between a first end and a second end is disposed within the internal branch and the inner lumen of tubular body of the prosthesis prior to delivery of the prosthesis and during delivery and deployment of the prosthesis. The second end of the guide wire extends distally from the distal opening of the tubular body, and the first end of the guide wire extends through the internal branch and the at least one fenestration such that a portion of the guide wire is externally disposed relative to the prosthesis. The externally disposed portion of the guide wire is bent back on itself to form an externally disposed loop. After forming the loop, the first end of the guide wire extends in a distal direction, externally relative to the prosthesis.

In a feature of this aspect, the first end of the guide wire is attached by a releasable fastening device to an exterior surface of the tubular body of the prosthesis during delivery and deployment of the prosthesis. In another feature of this aspect, the first end of the guide wire extends in a distal direction along the length of the prosthesis terminating at the user end of the device.

In a further feature, the at least one fenestration comprises two or more fenestrations. In an additional feature, the first end of the guide wire is attached by a releasable fastening device to a surface of the tubular body during delivery and deployment of the prosthesis.

In yet another feature, the loop has a length of about 3 cm to about 6 cm. In a further feature, the loop has a length greater than 3 cm and less than 8 cm.

In a third aspect of the invention, a method of accessing an internal branch of a vessel using an endoluminal prosthesis assembly having a pre-loaded guide wire comprises providing a delivery device comprising an endoluminal prosthesis assembly having a pre-loaded guide wire. The prosthesis assembly comprises a tubular body, an inner lumen extending between proximal and distal ends of the tubular body, at least one fenestration disposed in a sidewall of the tubular body, an internal branch at least partially formed with the sidewall of the body and disposed in parallel alignment with the prosthesis, and a pre-loaded guide wire. At least a portion of the guide wire extends through the inner lumen of the tubular body prior to delivery of and during delivery and deployment of the prosthesis assembly and at least a portion of the guide wire is disposed exterior to the tubular body prior to delivery of and during delivery and deployment of the prosthesis assembly. The portion of the guide wire disposed exterior to the tubular body is formed into a looping configuration. The method further comprises inserting the delivery device into the vessel having the internal branch being accessed and positioning the tubular body with the at the least one fenestration in alignment with the internal branch of the vessel, whereby the looping configuration of the preloaded guidewire is also aligned with the internal branch of the vessel; at least partially exposing the prosthesis assembly such that it expands radially toward the vessel walls; and advancing an auxiliary catheter over the preloaded guide wire until the auxiliary catheter reaches a bending point of the looping configuration; thereby aligning the auxiliary catheter with the internal branch of the vessel. The method further comprises delivering a branch guide wire through the auxiliary catheter thereby directing the branch guide wire to the internal branch of the vessel; and advancing an access catheter over the branch guide wire to introduce the access catheter to the internal branch.

In a feature of this aspect, the access catheter has a steerable proximal end portion. In another feature, the tubular body comprises at least two fenestrations. In an additional feature, the tubular body comprises an internal branch through which the preloaded guide wire extends.

BRIEF DESCRIPTION OF THE DRAWINGS

FIG. 2 depicts an embodiment of a prosthesis with pre-loaded guide wire having a looping configuration;

FIG. 3 depicts another embodiment of a prosthesis with pre-loaded guide wire having a looping configuration;

FIG. 4 depicts yet another embodiment of a prosthesis with pre-loaded guide wire having a looping configuration;

DETAILED DESCRIPTION

Figure 1:
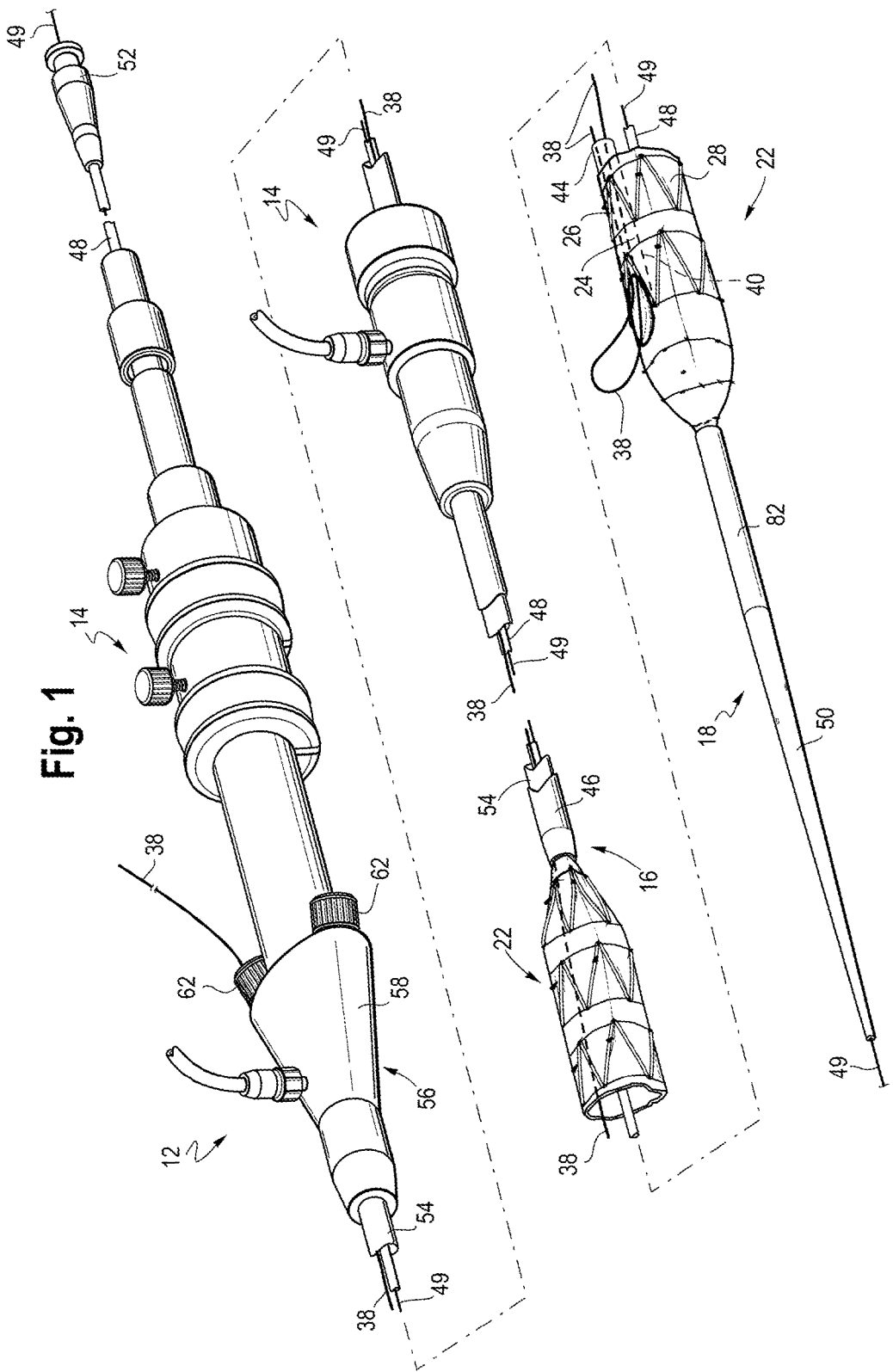
FIG. 1 depicts a device for delivering and deploying an endoluminal prosthesis.

In the present application, the term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the delivery device and the distal end of the prosthesis is that end that is closest to the operator end of the delivery device. When referring to the prosthesis relative to placement in the human body, the ends of the various devices and parts of devices may be referred to as the proximal or inflow end (that end that receives fluid first, and the distal or outflow end (that end from which the fluid exits).

Throughout the specification, unless the context requires otherwise, the words "comprise," "include," "and have," and variations such as "comprising," "including," and "having," imply the inclusion of an item or group of items, without the exclusion of any other item or group of items.

The term "prosthesis" means any device, object, or structure that supports, repairs, or replaces, or is configured to support, repair, or replace a body part or a function of that body part. It can also mean a device that enhances or adds functionality to a physiological system.

The term "stent" means any device or structure that provides or is configured to provide rigidity, expansion force, or support to a body part, for example, a diseased, damaged, or otherwise compromised body lumen. A stent may comprise any suitable biocompatible material, including, but not limited to fabrics, metals, plastics, and the like. Examples of suitable materials include metals such as stainless steel and nitinol, and plastics such as polyethylene terephthalate ("PET"), polytetrafluoroethylene ("PTFE") and polyurethane.

A stent may be "expandable," that is, it may be capable of being expanded to a larger-dimension configuration. A stent may expand by virtue of its own resilience (i.e., self-expanding), upon the application of an external force (i.e., balloon-expandable), or by a combination of both. In one example, a stent may have one or more self-expanding portions and one or more balloon-expandable portions. An example of a suitable self-expanding stent includes Z-STENTS®, which are available from Cook Inc., Bloomington, Ind., USA.

The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. A stent may be attached to or associated with a graft to form a "stent graft."

A graft material may comprise a biocompatible synthetic or biological material. Examples of suitable synthetic materials include fabrics, woven and non-woven materials, and porous and non-porous sheet materials. One exemplary synthetic graft material includes a woven polyester having a twill weave and a porosity of about 350 ml/min/cm.sup.2, and is available from VASCUTEK® Ltd., Renfrewshire, Scotland, UK. Other synthetic graft materials include biocompatible materials such as polyester, polytetrafluoroethylene (PTFE), polyurethane, and the like. Examples of suitable biological materials include, for example, pericardial tissue and extracellular matrix materials such as SIS.

Examples of suitable graft materials are described in U.S. Pat. Nos. 4,502,159, 4,675,361, 4,861,830, 4,902,508, 5,017,664, 5,733,337, 6,206,931, 6,358,284, 6,379,710, 6,666,892, 6,752,826, and 6,939,377, in U.S. Patent Application Publication Nos. 2002/0187288 A1 and 2003/0149471 A1, and in PCT Published Patent Application No. WO 98/22158, which are each incorporated by reference herein in their entirety.

The term "vessel" refers to a tube, cavity, duct, or canal in which fluid may be contained and conveyed or circulated. A body vessel (as opposed to a prosthetic vessel) is a vessel that exists naturally, or is formed naturally in the body. Examples of body vessels include, but are not limited to, blood vessels such as the aorta and the femoral artery, the esophagus, the trachea, the ureter, the bile duct, and the like. Examples of prosthetic vessels include, but are not limited to, stents, grafts, stent grafts, venous or aortal valves, vena cava filters, and the like.

The term "lumen" describes a space within a vessel in which fluid may be contained, conveyed, and/or circulated. The term "endoluminal" means within a lumen, and can refer to objects that are found or that can be placed within a lumen, or methods or processes that occur within a lumen. An "endoluminal prosthesis" is a prosthesis that is found or that can be placed within a lumen. Examples of endoluminal prostheses include, but are not limited to, stents, grafts, stent grafts, venous or aortal valves, vena cava filters, and the like. An endoluminal prosthesis may be generally tubular and comprise one or more lumens. Examples of tubular prostheses include, but are not limited to, straight, curved, branched, and bifurcated prostheses.

FIG. 1 shows a device 10 for delivering and deploying an endoluminal prosthesis 22 in a vessel of a patient. The device 10 includes a delivery catheter 12 comprising an operator end comprising an external manipulation section 14, a distal positioning mechanism or attachment region 16, and an introduction end comprising a proximal positioning mechanism or attachment region 18. The distal and proximal attachment regions 16, 18 are positioned inside the patient's body during a medical procedure, whereas the operator end having an external manipulation section 14 is positioned outside the patient's body. During a procedure, the physician controls or manipulates the external manipulation section 14 to position the proximal and distal attachment regions 18, 16 and to release the prosthesis 22 into the vessel.

The delivery and deployment device 10 includes an endoluminal prosthesis 22 disposed at a prosthesis retention region located at a proximal end portion of the delivery catheter 12 between the proximal and distal attachment regions 18, 16. The prosthesis 22 may comprise a tubular body 24 constructed of graft material 28, as described above. The prosthesis 22 may additionally or alternatively comprise one or more expandable stents 26 disposed at least partly coextensive with the graft material 28. Each stent 26 may be coupled to an interior and/or exterior surface of the tubular body 24. The prosthesis 22 shown in FIG. 1 comprises a graft material 28 and a plurality of expandable stents 26 disposed coextensive with the graft material 28.

The prosthesis 22 shown in FIG. 1 further comprises a fenestration 30 disposed in a sidewall 32 of the body 24 of the prosthesis 22, in particular, in the sidewall 32 between proximal and distal end openings 34, 36 of the tubular body 24. The fenestration 30 provides a fluid pathway through the sidewall 32 of the tubular body 24 and allows the prosthesis 22 to be placed in a main vessel in overlapping relationship with an intersecting branch vessel, without interrupting flow to the branch vessel.

The prosthesis 22 is disposed at a distal end portion of the delivery catheter 12. The prosthesis 22 is retained over the delivery catheter 12 by an elongate sheath 46. The sheath 46 comprises an elongate tubular body having an axial lumen (not shown). The sheath 46 extends proximally to the manipulation region 14. The prosthesis 22 is disposed within an axial lumen of the sheath 46 in a radially-compressed configuration. In FIG. 1, the prosthesis 22 is depicted in a partially deployed state, whereby the sheath 46 is partially retracted over the prosthesis 22, exposing the prosthesis 22 and allowing it to radially expand.

The sheath 46 preferably comprises a flexible structure that is able to bend and flex to negotiate complex and tortuous inner body lumina. The sheath 46 may comprise a biocompatible plastic such as PTFE, polyethylene, nylon, or the like. Examples of suitable sheath devices and materials are disclosed in U.S. Pat. Nos. 5,380,304, 6,589,227, and 7,025,758, and in U.S. Patent Application Publication Nos. 2001/0034514, 2002/0032408, and 2006/01555302, which are incorporated herein by reference in their entirety.

The delivery catheter shown in FIG. 1 further comprises an inner cannula 48 that extends proximally from the manipulation region 14 to the proximal attachment region 18. The inner cannula 48 has an axial lumen that is configured to receive a guide wire 49. A tapered extension 50 is coupled to the proximal end of the cannula 48 and forms the proximal end of the delivery catheter 12. Connection member 52 is coupled to the distal end of the cannula 48. Connection member 52 is adapted to accept a syringe and may be used to introduce reagents into the body lumen.

Cannula 48 is slidably disposed within the lumen of the sheath 46. The prosthesis 22 is retained over a proximal portion of the cannula 48 by the sheath 46. The cannula 48 is preferably flexible so that the device can be advanced within a relatively tortuous vessel, such as a femoral artery or the aortic arch. The cannula 48 may comprise metal, for example aluminum, stainless steel, or nitinol. The cannula 48 is in mechanical communication with the flexible extension 50. This allows the physician to control the flexible extension 50 remotely during a procedure. For example, the physician can rotate or slide the flexible extension 50 relative to the prosthesis 22 by manipulating the cannula 48.

The delivery device 10 shown in FIG. 1 further comprises an elongate tubular pusher 54 that extends proximally from the manipulation region 14 to the distal attachment region 16. The cannula 48 is slidably disposed within an axial lumen (not shown) of the pusher 54. The sheath 46 is slidably disposed over a proximal end portion of the pusher 54. The pusher 54 may comprise any suitable biocompatible material including metal or plastic. The pusher 54 may comprise a radiopaque material. Suitable materials include, but are not limited to aluminum, nitinol, nylon, polypropylene, and polyethylene. The pusher 54 preferably has high longitudinal column strength to ensure adequate energy transfer between the user and the prosthesis during deployment.

The proximal end of the pusher 54 is disposed adjacent the proximal end of the prosthesis 22. To deploy the prosthesis 22, the physician slides the sheath 46 distally while applying proximal pressure to the pusher 54 in the user manipulation region 14. The pusher 54 prevents the prosthesis 22 from sliding distally within the sheath 46 when the sheath is withdrawn. As a result, the sheath 46 retracts distally over the prosthesis 22, exposing the prosthesis, thereby allowing it to expand radially outwardly.

The distal end of the pusher 54 is connected to an auxiliary access device 56. The access device 56 comprises a housing 58, a channel 60 extending generally axially through the housing, and a port 62 coupled to the channel 60. The port 62 provides fluid and mechanical communication between the user manipulation section 14 and the channel 60, which provides fluid and mechanical communication with an axial lumen 64 of the pusher 54 which, in turn, provides fluid and mechanical communication with the prosthesis 22.

FIG. 2 depicts an endoluminal prosthesis assembly 20 in accordance with an embodiment of the present invention. The assembly 20 includes an endoluminal prosthesis having a tubular body 24 and a pre-loaded guide wire 38. In the embodiment shown in FIG. 2, the endoluminal prosthesis 22 is a stent graft comprising graft material 28 and a plurality of stents 26 disposed co-extensively with the graft material 28. The tubular body 24 has a proximal opening 34 at a proximal end and a distal opening 36 at a distal end. With reference to the delivery device 10, the proximal end is that end of the device that is toward the introduction end of the delivery device and the distal end is that end of the device that is toward the operator end of the delivery device. The prosthesis 22 includes at least one fenestration 30 disposed in the sidewall 32 of the graft material 28 of the body 24 between the proximal end and the distal end of the body. The fenestration 30 may be disposed at any location along the length of the prosthesis 22. In FIG. 2, the fenestration 30 is disposed proximal the proximal end of the tubular body 24. While the prosthesis 22 depicted in FIG. 2 includes one fenestration, it will be appreciated that alternative embodiments may include two or more fenestrations. For example, the prosthesis may comprise two, three, and/or four or more fenestrations.

The prosthesis 22 also includes an internal branch 40 at least partially formed with the graft material 28 of the body 24 and disposed in parallel alignment with the prosthesis 22. The internal branch 40 has a proximal end 42 near the fenestration 30 and a distal end 44 that extends toward the operator end of the delivery device 10. In exemplary embodiments, the proximal end 42 of the internal branch 40 can be adjacent to the fenestration 30.

The pre-loaded guide wire 38 has a proximal portion 66 comprising a first end 70 and a distal portion 68 comprising a second end 72. As shown in FIG. 2, in the pre-loaded state, the guide wire 38 extends in a distal direction from the distal opening 36 of the stent graft 22 and also extends at least partially through the lumen 78 of the stent graft 22 in a direction toward the delivery end of the device 10. The portion of the guide wire 38 entering the lumen 78 of the stent graft 22 extends through the internal branch 40, entering at the distal end 44 of the internal branch 40, exits the fenestration 30, loops back upon itself exteriorly to the stent graft 22 at or above the fenestration 30 and then reenters the fenestration 30 and extends in a distal direction through the internal branch 40 and then through the lumen 78 once the internal branch 40 terminates.

In the context of this invention, pre-loaded with the prosthesis 22 and the delivery device 10 means that at least a portion of the guide wire 38 is disposed within the internal branch 40 in the lumen 78 of the tubular body 24 of the prosthesis 22 prior to the introduction of the delivery device 10 into a body, during delivery and during deployment of the prosthesis 22. Hence, the prosthesis 22 and a portion of the guidewire 38 will be present in the device 10 and enclosed within the sheath 46 covering the device 10 prior to any use of the device 10 by a physician. The guide wire 38 has two ends 70, 72 and a portion between the ends. The second end 72 of the guide wire 38 will be at or near the operator end of the delivery device 10 and extends distally from the distal opening 36 of the tubular body 24. The first end 70 of the guide wire 38 slidably extends through the internal branch 40 and then out of the fenestration 30 and extends proximally away from the fenestration 30 such that the guide wire 38 is slidably disposed through the fenestration 30 with a portion 66 of the wire 38 disposed exterior to the prosthesis 22. This portion 66 of the guide wire 38 bends back on itself in a distal direction (toward the operator end) at a bending point such that it forms a looping configuration 80 adapted to retain the pre-loaded guide wire 38 in the prosthesis 22 during delivery and deployment of the prosthesis 22 and to provide a marker of branch vessel location. For example, the loop configuration 80 can be aligned with a branch vessel location when the stent graft 22 is placed such that an operator will have a physical indicator of the location of the branch vessel.

The looping configuration 80 of the guide wire 38 is exterior to the prosthesis 22. The length that the wire 38 extends from the fenestration 30 prior to bending at the bending point to form the looping configuration 80 varies based on the wire properties and on the anatomy of the patient. Exemplary properties affecting length of the loop configuration 80 include gauge length, stiffness, and material of construction. The length may range from about 2 cm to about 10 cm. For example, the length may range from about 3 cm to about 8 cm. Exemplary lengths may include 2 cm, 3 cm, 4 cm, 5 cm, 6 cm, 7 cm, 8 cm, 9 cm, and 10 cm. It will be appreciated that the length is approximately equal to the size of the loop formed in the looping configuration.

The wire 38 may be formed from any suitable material, such as a biocompatible metal or plastic, and with dimensions suitable for the particular application. In one example, a wire comprises a highly elastic metal, such as nitinol or the like, and has a diameter in the range of about 0.016 to about 0.018 inches. Wires made of other materials, and having other diameters are also contemplated.

The looping configuration 80 is adapted to retain the pre-loaded guide wire 38 in the prosthesis 22 during delivery and deployment of the prosthesis 22. Additionally, the guide wire 38 is also at least partially retained by static friction created between the cannula 48, the prosthesis 22 and the sheath 46 when the delivery and deployment device 10 is assembled prior to delivery and then during delivery and deployment until the sheath 46 is pulled back from the prosthesis 22 and the static friction is removed.

In FIG. 2, after the wire 38 forms a looping configuration 80, the first end 70 of the guide wire 38 re-enters the internal branch 40 in the tubular body 24 of the prosthesis 22 via the same fenestration 30 from which it previously exited. The looping configuration 80 and the static friction aid in retaining the guide wire 38 in place during delivery and deployment of the prosthesis 22. Additionally, a releasable fastening device 76 may be used to aid in retaining the guide wire 38. The releasable fastening device 76 may attach the guide wire 38 to a surface of the tubular body 24. When the first end 70 of the guide wire 38 is re-introduced to the internal branch 40 in the lumen 78 of the tubular body 24, the releasable fastening device 76 can attach the guide wire 38 to the interior surface of the tubular body 24. An exemplary releasable fastening device 76 may comprise a suture attached to the surface of the tubular body 24 and engaged around the guide wire 38 whereby upon retraction of the guide wire 38, the suture is released from engagement therewith.

In addition to aiding in retaining the pre-loaded guide wire 38 in the prosthesis 22 during deployment and delivery, the looping configuration 80 of the guide wire 38 advantageously aids a physician in cannulating a branch vessel by providing a physical marker for the location of the branch vessel. It can be difficult for a physician to quickly and accurately determine the location of the target branch vessel when trying to cannulate the same. The looping configuration 80 of the wire guide 38 provides an indicator or marker of the location of the branch vessel in the form of a hard stopping point for a cannula being advanced to the target branch vessel. The hard stopping point aids a physician in accurately determining the location of the branch vessel in order to more safely, efficiently and effectively cannulate the fenestration 30 and the target branch vessel.

FIG. 3 depicts an alternative embodiment of an endoluminal prosthesis assembly 120 in accordance with the present invention. The assembly 120 includes an endoluminal prosthesis 122 having a tubular body 124 and a pre-loaded guide wire 138. In the embodiment shown in FIG. 3, the endoluminal prosthesis 122 is a stent graft comprising graft material 128 and a plurality of stents 126 disposed co-extensively with the graft material. The tubular body 124 has a proximal opening 134 at a proximal end and a distal opening 136 at a distal end. The prosthesis 122 includes at least one fenestration 130 disposed in the sidewall 132 of the graft material 128 of the body 124 between the proximal opening 134 and the distal opening 136 of the body 124. The fenestration 130 may be disposed at any location along the length of the prosthesis 122. In FIG. 3, the fenestration 130 is disposed proximal the proximal end of the tubular body. While the prosthesis depicted in FIG. 3 includes one fenestration, it will be appreciated that alternative embodiments may include two or more fenestrations. For example, the prosthesis may comprise two, three, and/or four or more fenestrations.

The prosthesis 122 also includes an internal branch 140 at least partially formed with the graft material 128 of the body 124 and disposed in parallel alignment with the prosthesis 122. The internal branch 140 has a proximal end 142 near the fenestration 130 and a distal end 144 that extends toward the operator end of the delivery device 10. In exemplary embodiments, the proximal end 142 of the internal branch 140 can be adjacent to the fenestration 130.

The pre-loaded guide wire 138 has a proximal portion 166 comprising a first end 170 and a distal portion 168 comprising a second end 172. As shown in FIG. 3, in the pre-loaded state, the distal portion 168 of the guide wire 138 extends in a distal direction from the distal opening 136 of the stent graft 122. The proximal portion 166 of the guide wire 122 extends at least partially through the lumen 178 of the stent graft 122 prior to entering the distal end 144 of the internal branch 140 and extending through the internal branch 140, then exits the fenestration 130, loops back upon itself exteriorly to the stent graft 122 above the fenestration 130 and above the proximal opening 134 of the prosthesis 122 and then reenters the lumen 178 of the prosthesis 122 through the proximal end 134 of the tubular body 124.

In FIG. 3, after the wire 138 forms a looping configuration 180, the first end 170 of the guide wire 138 re-enters the lumen 180 of the prosthesis 122 via the proximal opening 134 of the tubular body 124. The looping configuration 180 aids in retaining the guide wire 138 in place during delivery and deployment of the prosthesis 122. Additionally, a releasable fastening device may be used to aid in retaining the guide wire 138. The releasable fastening device may attach the guide wire 138 to a surface of the tubular body 124. When the first end 170 of the guide wire 138 is re-introduced to the lumen 178 of the tubular body 124, the releasable fastening device can attach the guide wire 138 to the interior surface of the tubular body 124. An exemplary releasable fastening device may comprise a suture attached to the surface of the tubular body 124 and engaged around the guide wire 138 whereby upon retraction of the guide wire 138, the suture is released from engagement therewith.

In addition to aiding in retaining the pre-loaded guide wire 138 in the prosthesis 122 during deployment and delivery, the looping configuration 180 of the guide wire 138 advantageously aids a physician in cannulating a branch vessel by providing a physical marker for the location of the branch vessel. It can be difficult for a physician to quickly and accurately determine the location of the target branch vessel when trying to cannulate the same. The looping configuration 180 of the wire guide 138 provides an indicator or marker of the location of the branch vessel in the form of a hard stopping point for a cannula being advanced to the target branch vessel. The hard stopping point aids a physician in accurately determining the location of the branch vessel in order to more safely, efficiently and effectively cannulate the fenestration 130 and the target branch vessel.

FIG. 4 depicts another alternative embodiment of an endoluminal prosthesis assembly 220 in accordance with the present invention. The assembly 220 includes an endoluminal prosthesis 222 having a tubular body 224 and a pre-loaded guide wire 238. In the embodiment shown in FIG. 4, the endoluminal prosthesis 222 is a stent graft comprising graft material 228 and a plurality of stents 226 disposed co-extensively with the graft material 228. The tubular body 224 has a proximal opening 234 at a proximal end and a distal opening 236 at a distal end. The prosthesis 222 includes at least one fenestration 230 disposed in the sidewall of the graft material 228 of the body 224 between the proximal opening 234 and the distal opening 236 of the body 224. The fenestration 230 may be disposed at any location along the length of the prosthesis 222. In FIG. 4, the fenestration 230 is disposed proximal the proximal opening 234 of the tubular body 224. While the prosthesis 222 depicted in FIG. 4 includes one fenestration, it will be appreciated that alternative embodiments may include two or more fenestrations. For example, the prosthesis may comprise two, three, and/or four or more fenestrations.

The prosthesis 222 also includes an internal branch 240 at least partially formed with the graft material 228 of the body 224 and disposed in parallel alignment with the prosthesis 222. The internal branch 240 has a proximal end 242 near the fenestration 230 and a distal end 244 that extends toward the operator end of the delivery device.

The assembly 220 also includes a guide wire 238 having a proximal portion 266 comprising a first end 270 and a distal portion 268 comprising a second end 272. As shown in FIG. 4, in the pre-loaded state, the distal portion 268 of the guide wire 238 extends in a distal direction from the distal opening 236 of the prosthesis 222. The proximal portion 266 of the guide wire 238 extends at least partially through the lumen 278 of the prosthesis 222 prior to entering the distal end 244 of the internal branch 240 and extending through the internal branch 240, then exits the fenestration 230, bends back upon itself exteriorly to the stent graft 222 at or above the fenestration 230 and extends alongside the exterior of the prosthesis 222. The proximal portion 266 of the guide wire 238 may extend along a portion of the length of prosthesis 222, terminating prior to the end of the prosthesis 222 or may extend in a distal direction to the operator end of the device. In exemplary embodiments, the proximal portion 266 of the wire 238 may extend for a length of about 2 to 120 centimeters.

In FIG. 4, after the wire 238 forms a looping configuration 280, the first end 270 of the guide wire 238 extends along the exterior of the prosthesis 222. The looping configuration 280 aids in retaining the guide wire 238 in place during delivery and deployment of the prosthesis 222. Additionally, a releasable fastening device may be used to aid in retaining the guide wire 238. The releasable fastening device may attach the guide wire 238 to an exterior surface of the tubular body 224. When the first end 270 of the guide wire 238 extends along the exterior length of the tubular body 224, the releasable fastening device can attach the guide wire 238 to the exterior surface of the tubular body 224. An exemplary releasable fastening device may comprise a suture attached to the surface of the tubular body 224 and engaged around the guide wire 238 whereby upon retraction of the guide wire 238, the suture is released from engagement therewith.

In addition to aiding in retaining the pre-loaded guide wire 238 in the prosthesis 222 during deployment and delivery, the looping configuration 280 of the guide wire 238 advantageously aids a physician in cannulating a branch vessel by providing a physical marker for the location of the branch vessel. It can be difficult for a physician to quickly and accurately determine the location of the target branch vessel when trying to cannulate the same. The looping configuration of the wire guide provides an indicator or marker of the location of the branch vessel in the form of a hard stopping point for a cannula being advanced to the target branch vessel. The hard stopping point aids a physician in accurately determining the location of the branch vessel in order to more safely, efficiently and effectively cannulate the fenestration and the target branch vessel.

FIGS. 5-9 depict various stages of a method for delivering and deploying a prosthesis 22 comprising a fenestration 30 having a pre-loaded guide wire 38 with a looped configuration 80 into the aorta. Although the method is described in relation to a device for treating the aorta, it can readily be applied to other devices and indications.

A delivery catheter 12, as described for example with respect to FIG. 1, is provided and comprises a pusher 54 and an inner cannula 48 slidingly disposed within an axial lumen of the pusher 54. The delivery catheter 12 is slidingly disposed within an axial lumen of sheath 46. Prosthesis 22 is disposed over a distal end portion of the delivery catheter 12 within the axial lumen of sheath 46. A top cap 82 retains a distal end portion of the prosthesis 22 to prevent premature radial expansion of the distal end of the prosthesis as the sheath 46 is retracted proximally over the delivery catheter 12. Although not shown in FIGS. 5-9, the prosthesis 22 may comprise one or more expandable stents, as described above.

Figure 5:
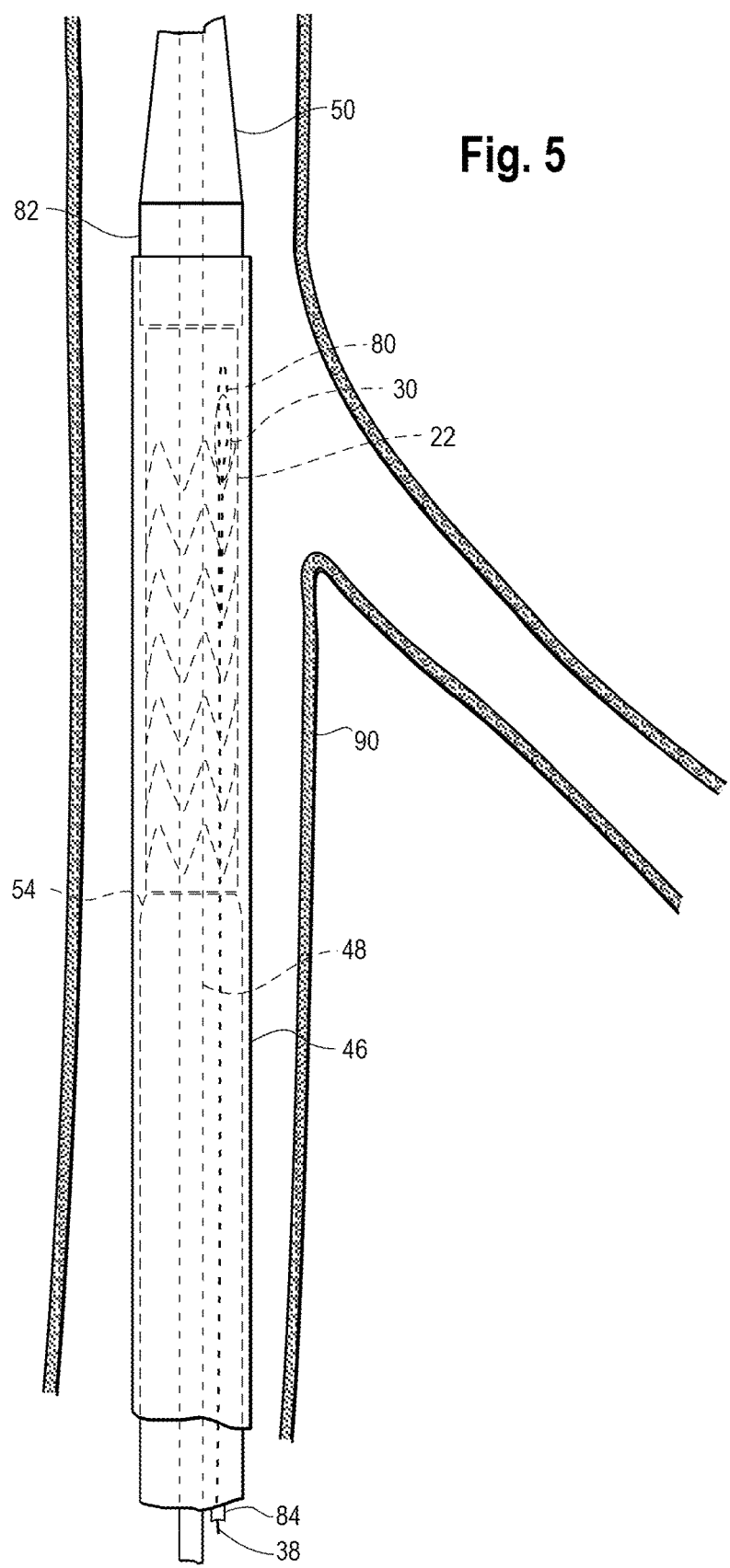
FIGS. 5-9 depict various stages of a method of using a delivery and deployment device including a prosthesis with pre-loaded guide wire having a looping configuration.

FIG. 5 depicts the delivery and deployment device 10 disposed in an un-deployed configuration within a vessel 90 (such as the aorta). The device 10 comprises the prosthesis 22 of FIG. 2, having a single fenestration 30 sized and configured to provide fluid communication between the lumen 78 of the prosthesis 22 and a branch vessel 92 (such as renal arteries) after the prosthesis 22 is deployed. Consequently, the prosthesis 22 can be placed within vessel 90 so that it overlaps a branch vessel 92 without occluding the branch vessel. The prosthesis 22 comprises a fenestration 30 having a pre-loaded guide wire 38 in a looping configuration 80 as described above. A portion of the guide wire 38 is disposed within the tubular body 24 of the prosthesis 22 during delivery and deployment of the prosthesis 22. The second end 72 of the guide wire (not shown) extends distally from the distal opening 36 of the tubular body 24 toward the user end of the device. The looping configuration 80 is formed by the first end 70 of the guide wire 38 slidably exiting the fenestration 30, extending proximally away from the fenestration 30 and then bending back on itself in a distal direction at a bending point such that the proximal portion 166 of the guide wire 38 forms a looping configuration 80. In this embodiment, the proximal portion 66 of the wire 38 reenters the fenestration 30, extends through the internal branch 40 and enters the lumen 78 of the prosthesis 22, where it may or may not be attached to the interior wall of the tubular body 24. The looping configuration 80 is exterior to the prosthesis 22. The length that the wire 38 extends from the fenestration 30 prior to bending at the bending point to form the looping configuration 80 varies based on the wire properties and on the anatomy of the patient.

The delivery catheter 12 may be delivered within the vessel 90 in a conventional manner. A guide wire (not shown) is introduced, for example, into a femoral artery and advanced into the vessel until the tip of the guide wire extends beyond the region in which the prosthesis 22 will be placed. The delivery and deployment device 10 is then inserted over the guide wire 49, via inner cannula 48, into the vessel 90 and positioned by radiographic techniques generally known in the art.

At this stage, the prosthesis 22 is disposed in a compressed configuration within the top cap 82 and an axial lumen of the sheath 46. As described above, at least a portion of the pre-loaded guide wire 38 is disposed within the lumen 78 of the tubular body 24 of the prosthesis 22 prior to the introduction of the delivery device 10 into a body, during delivery and during deployment of the prosthesis 22. An auxiliary catheter 84 may be provided and inserted over the guide wire 38 and into an axial lumen of the delivery catheter 12.

Figure 6:
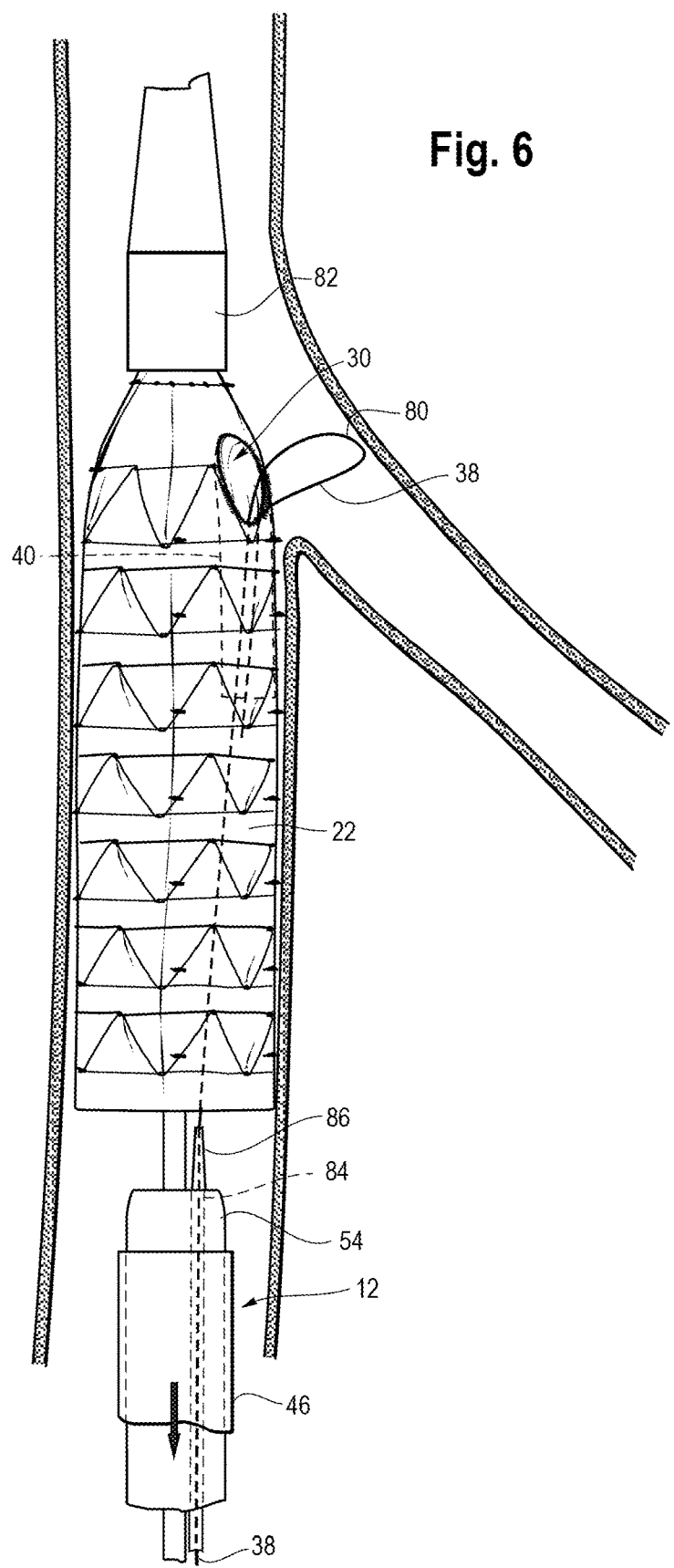

The delivery and deployment device 10 is positioned within the vessel by radiographic means so that the prosthesis 22 overlaps the ostia of, and fenestration 30 aligns with, a branch vessel 92. Once the device 10 is in a proper position, the sheath 46 is retracted to expose the prosthesis 22. This action releases the prosthesis 22 so that it can expand radially towards the vessel walls, as shown in FIG. 6. The top cap 82 retains the proximal end of the prosthesis 22, however, and prevents it from expanding at this stage. The physician may release the proximal end of the prosthesis 22 at a desired stage by sliding the top cap 82 proximally with respect to the prosthesis 22.

Figure 7:
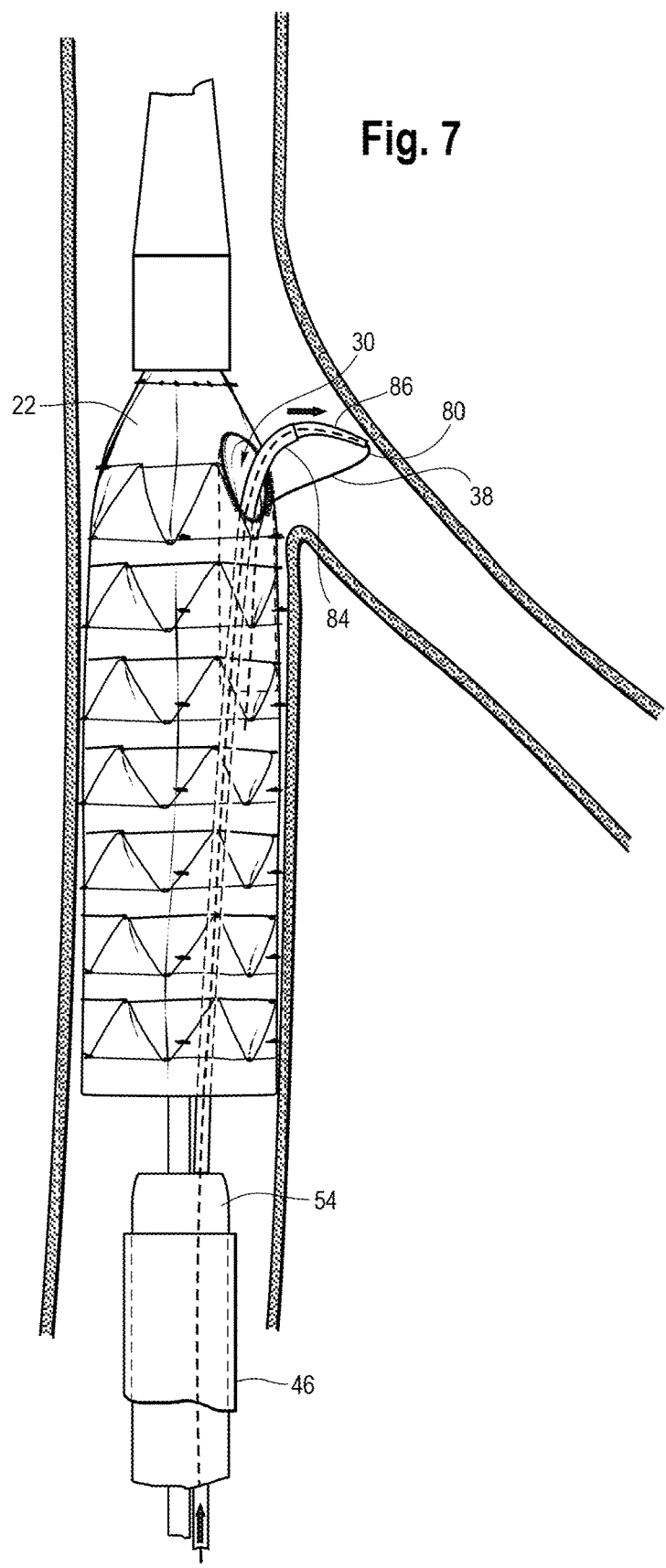
Figure 8:
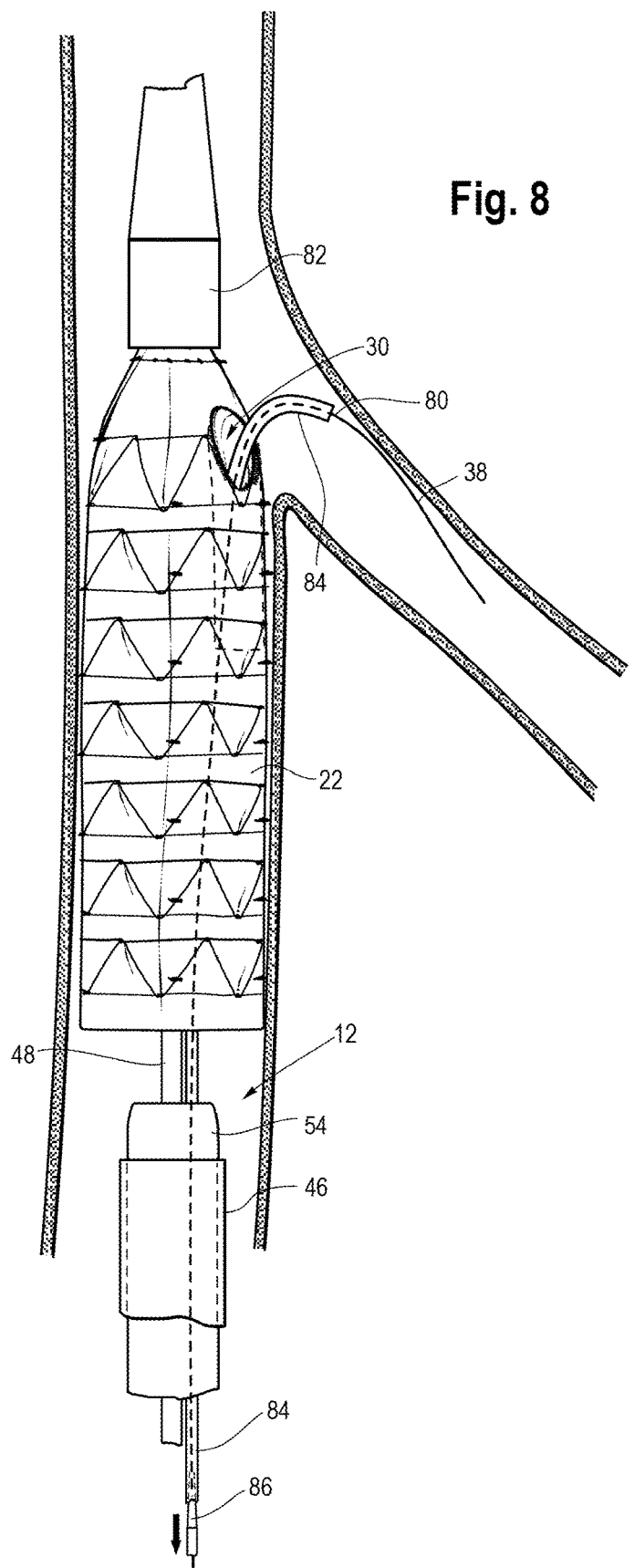

In FIG. 7, auxiliary catheter 84 is advanced proximally over the wire 38 through the lumen of the prosthesis 22 and the internal branch 40 of the prosthesis until the proximal end of catheter 84 passes through the fenestration 30 and reaches the bending point of the looping configuration 80. The looping configuration 80 provides a hard stop that indicates the location of the branch vessel. The looping configuration 80 provides a physical indication in addition to a radiographic indication for the physician. Such physical indication is advantageous in providing a safe and efficient procedure for the patient. In FIG. 8, the dilator 86 of the auxiliary catheter 84 has been removed by withdrawing it distally through the sheath 84.

Figure 9:
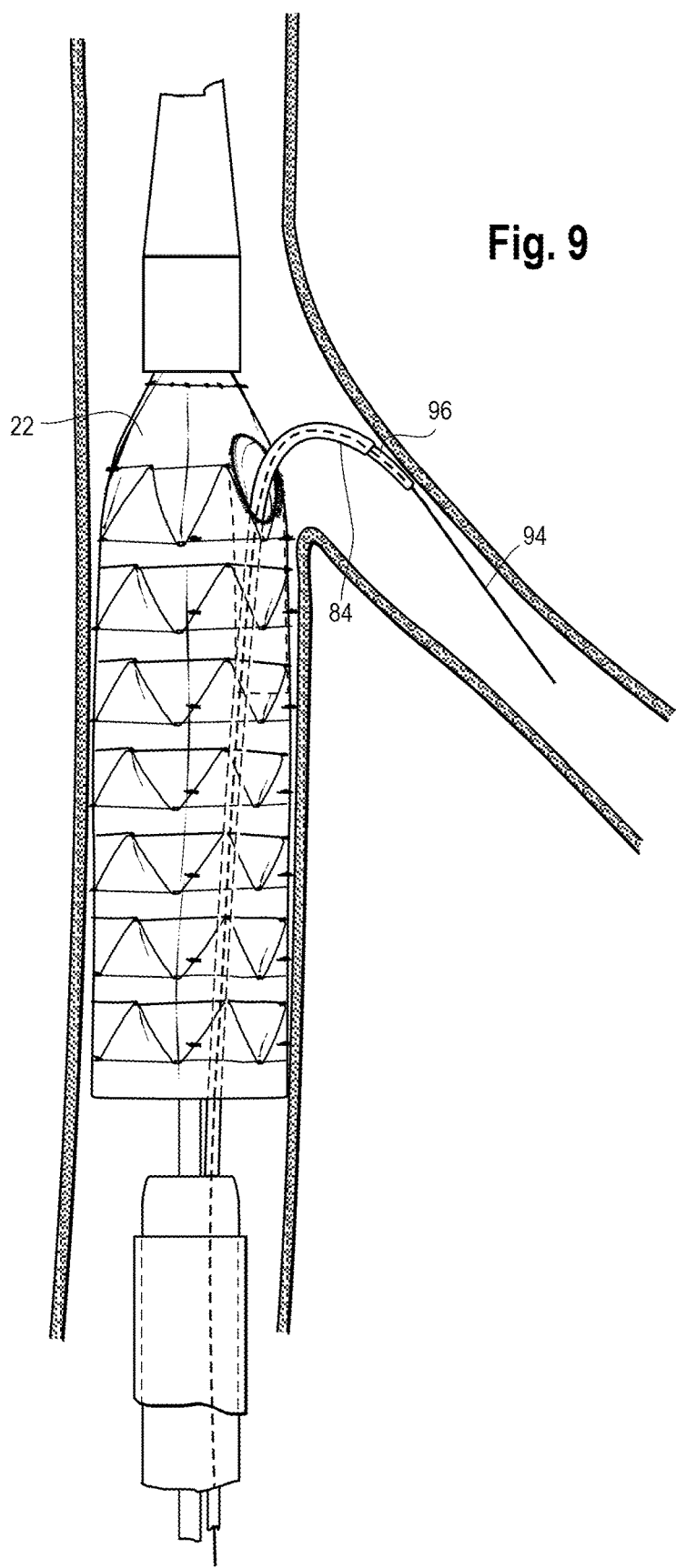

Next, a branch guide wire 94 is provided for cannulating the branch vessels. As shown in FIG. 9, the branch guide wire 94 is delivered through sheath 84 alongside the proximal portion of the wire 38 comprising the looping configuration 80. A branch access catheter 96 is then introduced over the guide wire 94. The access catheter 96 preferably has a steerable proximal end portion that can be used to guide the branch wires 94 through the fenestration 30 and into the branch vessel 92. Suitable catheters are commercially available and include the Torcon NB®. Advantage Catheters are available from Cook, Inc., Bloomington Ind., USA.

Once the branch vessel is cannulated, the catheter 96 is removed, by withdrawing it distally through sheath 84. At this point, the preloaded wire 38 is no longer needed and may be removed by pulling distally on the second end of the wire 38 until the proximal portion of the wire 38, including the un-looped looping configuration, exits the device 10.

With the guide wire 94 in place, the physician may deliver one or more interventional catheters (including, for example, catheters carrying balloons, stents, grafts, imaging devices, and the like) into the branch vessel 92 through the fenestration 30.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together.

The invention claimed is:

1. An endoluminal prosthesis assembly comprising
a delivery system having an introduction end, an operator end, and a stent graft retention region;
an endoluminal prosthesis disposed at the stent graft retention region, the prosthesis comprising a tubular body, an inner lumen extending between proximal and distal ends of the tubular body, a proximal opening at the proximal end, a distal opening at the distal end, at least one fenestration disposed in a sidewall of the tubular body between the proximal and distal ends, and an internal branch at least partially formed with the sidewall of the tubular body and disposed in parallel alignment with the prosthesis, wherein the proximal end of the tubular body is toward the introduction end and the distal end of the tubular body is toward the operator end; and
a guide wire pre-loaded with the prosthesis in the delivery system and configured to receive an auxiliary catheter moveable over the guide wire, at least a portion of the guide wire between a first end and a second end disposed within the internal branch and the inner lumen of the prosthesis prior to delivery of the prosthesis and during delivery and deployment of the prosthesis, the second end of the guide wire extending distally from the distal opening of the tubular body, the first end of the guide wire extending through the internal branch and the at least one fenestration such that a portion of the guide wire is externally disposed relative to the prosthesis, wherein the externally disposed portion of the guide wire is bent back on itself to form an externally disposed loop extending proximally away from the at least one fenestration, and wherein after forming the loop, the first end of the guide wire re-entering the tubular body of the prosthesis such that the first end of the guide wire is disposed internally relative to the prosthesis, and
wherein the loop provides a hard stop for the auxiliary catheter.

2. The assembly of claim 1, wherein the first end of the guide wire is attached by a releasable fastening device to an interior surface of the tubular body during delivery and deployment of the prosthesis.

3. The assembly of claim 2, wherein the releasable fastening device is a suture.

4. The assembly of claim 1, wherein the first end of the guide wire re-enters the tubular body of the prosthesis through the proximal opening of the tubular body.

5. The assembly of claim 1, wherein the first end of the guide wire re-enters the tubular body of the prosthesis through the at least one fenestration from which it exited.

6. The assembly of claim 1, wherein the at least one fenestration comprises two or more fenestrations.

7. The assembly of claim 1, wherein the loop has a length of about 3 cm to about 6 cm.

8. The assembly of claim 1, wherein the loop has a length greater than 3 cm and less than 8 cm.

9. The assembly of claim 1, wherein the guide wire comprises nitinol.

10. An endoluminal prosthesis assembly comprising
a delivery system having an introduction end, an operator end, and a stent graft retention region;
an endoluminal prosthesis disposed at the stent graft retention region, the prosthesis comprising a tubular body, an inner lumen extending between proximal and distal ends of the tubular body, at least one fenestration disposed in a sidewall of the tubular body between the proximal and distal ends, and an internal branch at least partially formed with the sidewall of the tubular body and disposed in parallel alignment with the prosthesis, wherein the proximal end of the tubular body is toward the introduction end and the distal end of the tubular body is toward the operator end; and
a guide wire pre-loaded with the prosthesis in the delivery system and configured to receive an auxiliary catheter moveable over the guide wire, at least a portion of the guide wire between a first end and a second end disposed within the internal branch and the inner lumen of tubular body of the prosthesis prior to delivery of the prosthesis and during delivery and deployment of the prosthesis, the second end of the guide wire extending distally from the distal opening of the tubular body, the first end of the guide wire extending through the internal branch and the at least one fenestration such that a portion of the guide wire is externally disposed relative to the prosthesis, wherein the externally disposed portion of the guide wire is bent back on itself to form an externally disposed loop extending proximally away from the at least one fenestration, and wherein after forming the loop, the first end of the guide wire extends in a distal direction, externally relative to the prosthesis, and
wherein the loop provides a hard stop for the auxiliary catheter.

11. The assembly of claim 10, wherein the first end of the guide wire is attached by a releasable fastening device to an exterior surface of the tubular body of the prosthesis during delivery and deployment of the prosthesis.

12. The assembly of claim 10, wherein the first end of the guide wire extends in a distal direction along the length of the prosthesis terminating at the user end of the device.

13. The assembly of claim 10, wherein the at least one fenestration comprises two or more fenestrations.

14. The assembly of claim 10, wherein the first end of the guide wire is attached by a releasable fastening device to a surface of the tubular body during delivery and deployment of the prosthesis.

15. The assembly of claim 10, wherein the loop has a length of about 3 cm to about 6 cm.

16. The assembly of claim 10, wherein the loop has a length greater than 3 cm and less than 8 cm.

* * * * *